United States Patent
Patel et al.

(10) Patent No.: US 10,781,147 B2
(45) Date of Patent: Sep. 22, 2020

(54) METHODS FOR TOLUENE RECOVERY FROM LINEAR ALPHA OLEFIN PRODUCTION

(71) Applicant: SABIC Global Technologies B.V., Bergen op Zoom (NL)

(72) Inventors: Haresh Patel, Ahmedabad (IN); Saad Ayed Al-Qahtani, Jubail (SA); Fahad Mubark Al-Khaldi, Jubail (SA); Rajan V. Deshmukh, Jubail (SA); Aref Mana Seneg Al-Shugaih, Jubail (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 274 days.

(21) Appl. No.: 16/060,736

(22) PCT Filed: Dec. 21, 2016

(86) PCT No.: PCT/IB2016/057887
§ 371 (c)(1),
(2) Date: Jun. 8, 2018

(87) PCT Pub. No.: WO2017/109725
PCT Pub. Date: Jun. 29, 2017

(65) Prior Publication Data
US 2019/0002365 A1    Jan. 3, 2019

Related U.S. Application Data

(60) Provisional application No. 62/271,119, filed on Dec. 22, 2015.

(51) Int. Cl.
*C07C 2/08* (2006.01)
*B08B 9/08* (2006.01)

(52) U.S. Cl.
CPC .................. *C07C 2/08* (2013.01); *B08B 9/08* (2013.01); *B08B 2220/04* (2013.01)

(58) Field of Classification Search
None
See application file for complete search history.

(56) References Cited

U.S. PATENT DOCUMENTS 3,797,690 A    3/1974  Taylor et al.
4,360,606 A    11/1982 Tobias et al.
(Continued)

FOREIGN PATENT DOCUMENTS

EP    1749808 A1    2/2007
EP    1752212 A1    2/2007

OTHER PUBLICATIONS

International Search Report for International Application No. PCT/IB2016/057887; dated May 29, 2017; 6 pages.
(Continued)

*Primary Examiner* — Nicole Blan
(74) *Attorney, Agent, or Firm* — Norton Rose Fulbright US LLP

(57) ABSTRACT

The present disclosure provides a method of flushing a reactor used in the production of linear alpha olefins, including flushing reactor equipment with toluene from a solvent source, wherein the reactor contains by-products from the production of the linear alpha olefins, wherein the by-products include a polymeric material. The flushed toluene containing polymeric material is directed into a separation train containing the linear alpha olefins, wherein the polymeric material is soluble in at least one of the linear alpha olefins. The linear alpha olefins can be separated from the toluene and the toluene is recycled to the solvent source.

20 Claims, 1 Drawing Sheet

(56) References Cited

U.S. PATENT DOCUMENTS

| 5,523,508 | A | * | 6/1996 | Krawczyk | C07C 2/08 585/315 |
|---|---|---|---|---|---|
| 2012/0029258 | A1 | | 2/2012 | Wohl et al. | |
| 2014/0171707 | A1 | | 6/2014 | Nyce et al. | |
| 2014/0179970 | A1 | | 6/2014 | Fritz et al. | |
| 2016/0325263 | A1 | | 11/2016 | Uhm et al. | |

OTHER PUBLICATIONS

Written Opinion of the International Search Report for International Application No. PCT/IB2016/057887; dated May 29, 2017; 6 pages.

* cited by examiner

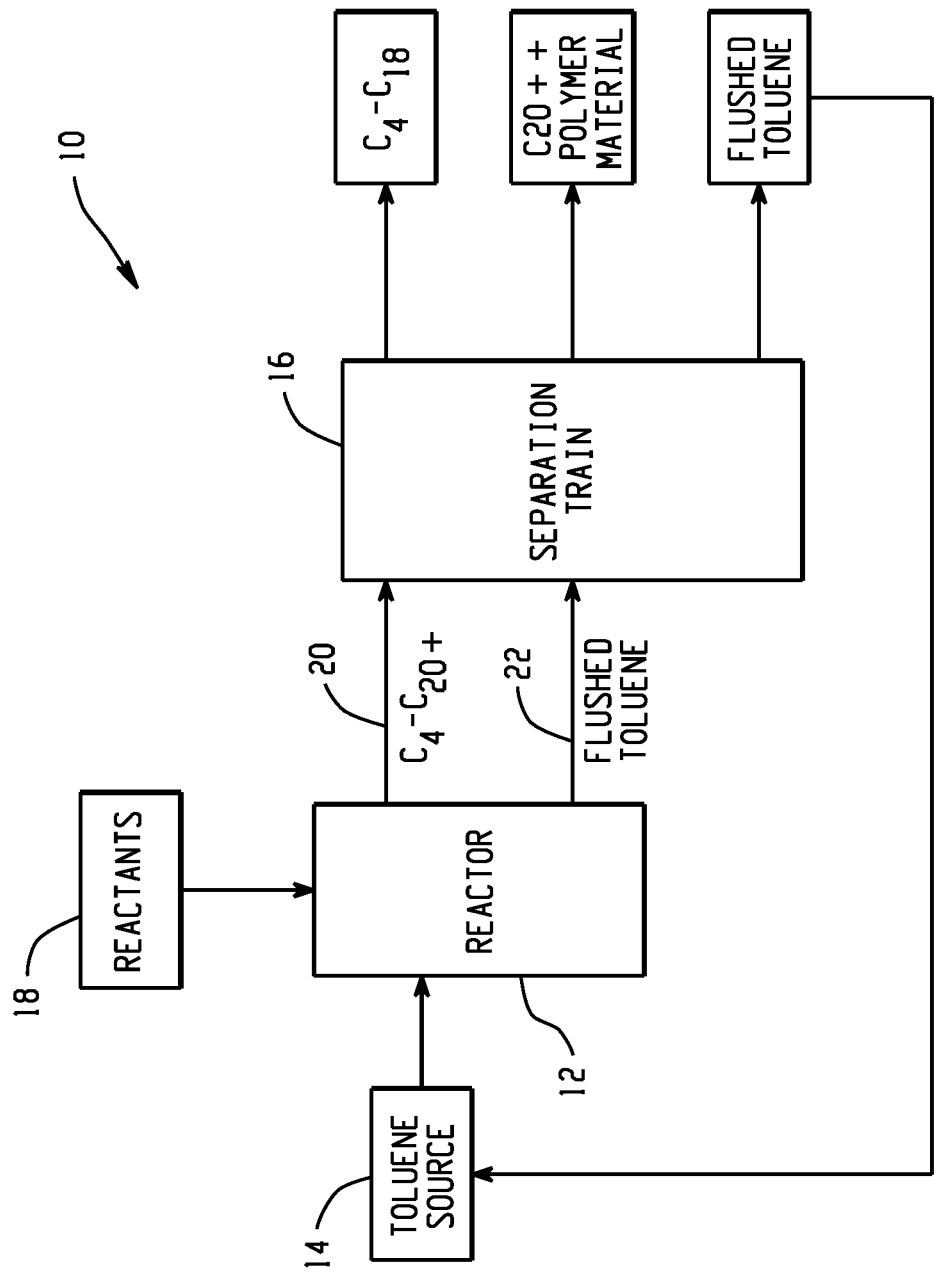

METHODS FOR TOLUENE RECOVERY FROM LINEAR ALPHA OLEFIN PRODUCTION

CROSS REFERENCE TO RELATED APPLICATIONS

This application is a 371 of International Application No. PCT/M2016/057887, filed Dec. 21, 2016, which claims priority to U.S. Application No. 62/271,119, filed Dec. 22, 2015, both of which are incorporated herein by reference in their entirety.

BACKGROUND

Linear olefins are one of the most useful classes of hydrocarbons used as raw materials in the petrochemical industry and among these the linear alpha-olefins, unbranched olefins whose double bond is located at a terminus of the chain, form an important subclass. Linear alpha olefins can be converted to linear primary alcohols by hydroformylation. Hydroformylation can also be used to prepare aldehydes as the major products which in turn can be oxidized to afford synthetic fatty acids, especially those with an odd carbon number, useful in the production of lubricants. Linear alpha olefins are also used in the most important class of detergents for domestic use, namely the linear alkylbenzenesulfonates, which are prepared by Fiedel-Crafts reaction of benzene with linear olefins followed by sulfonation.

Although linear olefins are the product of dehydrogenation of linear alkanes, the major portion of such products consists of the internal olefins. Preparation of alpha olefins is based largely on oligomerization of ethylene, which has a corollary that the alpha-olefins produced have an even number of carbon atoms. Oligomerization processes for ethylene are based mainly on organoaluminum compounds or transition metals as catalysts.

Oligomerization methods for preparing linear alpha-olefins are widely known in the art. These methods are typically carried out in the presence of a catalyst preferably comprising a zirconium component, such as zirconium tetraisobutyrate, and an aluminum component as activator, such as ethyl aluminum sesquichloride.

One problem associated with such oligomerization methods is that not only liquid linear alpha-olefins with desired chain length, e.g., C4-C18, are prepared, but also high molecular weight oligomers, C18-C20+. The high molecular weight oligomers and polymeric by-products of the oligomerization may be solid at reaction temperatures of 60 to 100° C. and have to be removed from the reactor equipment to avoid plugging the system equipment.

As a result, the oligomerization or polymerization plant has to be cleaned to remove the fouling and plugging at the reactor walls and walls of the piping. The cleaning is usually achieved by flushing the piping and the reactor equipment with a hot flushing medium. The flushing medium may be any solvent or white oil.

The flushing of piping and reactor equipment results in significant quantities of contaminated flushing media which are to be disposed in a difficult and cost-intensive manner. Additionally, flushing of piping and equipment is especially relevant for the plant sections containing reactive organoaluminum components, such as aluminum alkyls, which act as a co-catalyst or activator. It is important to remove the organoaluminum components completely before the reactor equipment or piping is opened and exposed to atmosphere.

Linear alpha olefins, particularly those of eight carbons or less, are used as co-monomers in the production of high density polyethylene and linear low density polyethylene.

In the linear alpha olefin manufacturing process, toluene is used as a solvent for flushing reactor equipment. Specifically, toluene is used to dissolve the polymer by-products deposited in the reactor equipment. A portion of the toluene is separated, recovered, and recycled for subsequent flushing, wherein another portion of the toluene containing the polymer material is discarded. However, after multiple cycles of flushing with the recycled toluene, the quality of the toluene is deteriorated over time and must be regenerated, which adds to the overall operation costs.

In certain examples, a separate toluene recovery unit may be used to purify and recover the toluene. However, with each round of flushing the reactor equipment, at least 10-20% of the toluene is removed along with the polymer by-product. As a result, even when using the toluene recovery unit, only 80-90% of the toluene can be recovered.

Therefore, there is a need for improved methods of toluene recovery used in flushing reactor equipment used in the production of linear alpha olefins.

BRIEF DESCRIPTION

The above described and other features are exemplified by the following FIGURES and detailed description.

A method of flushing a reactor used in the production of linear alpha olefins, comprising: flushing reactor equipment used in the production of linear alpha olefins, with toluene from a solvent source, wherein the reactor contains by-products from the production of the linear alpha olefins, wherein the by-products include a polymeric material; directing the flushed toluene containing polymeric material into a separation train containing the linear alpha olefins, wherein the polymeric material is soluble in at least one of the linear alpha olefins; separating the linear alpha olefins from the toluene; and recycling the toluene to the solvent source.

A method for producing linear alpha olefins, comprising: feeding ethylene, a solvent, and a catalyst into a reactor; oligomerizing ethylene in the reactor to produce linear alpha olefins and a polymeric material; directing the reactor effluent comprising the linear alpha olefins, solvent, and unreacted ethylene into a separation train configured to separate the linear alpha olefins from the solvent and unreacted ethylene; flushing the reactor with toluene from a toluene source, wherein the flushed toluene contains the polymeric material; directing the flushed toluene into the separation train, wherein the polymeric material is soluble in at least one of the linear alpha olefins; recycling the toluene to the toluene source; and recycling the separated unreacted ethylene and solvent to the reactor.

The above described and other features are exemplified by the following FIGURES and detailed description.

BRIEF DESCRIPTION OF THE DRAWINGS

Refer now to the FIGURES, which are exemplary embodiments, and wherein the like elements are numbered alike.

FIG. 1 is a schematic of an embodiment of the system disclosed herein.

DETAILED DESCRIPTION

The present disclosure provides systems and methods for flushing a reactor used in the production of linear alpha olefins. The reactor equipment can be flushed with toluene to remove any polymeric material by-product from the production of the linear alpha olefins. The flushed toluene comprising the polymeric material can be directed into a separation train comprising the linear alpha olefin reaction products. The polymeric material is soluble in at least one of the linear alpha olefins, such that the flushed toluene can exit the separation train essentially free of the polymeric material and can be recycled back to the toluene source for subsequent flushing of the reactor. The flushed toluene exiting the separation train can include less than or equal to 150 ppm, for example, less than or equal to 100 ppm, for example, less than or equal to 80 ppm, for example, less than or equal to 60 ppm, for example, less than or equal to 50 ppm of the polymeric material.

Linear alpha olefins (LAOs) are olefins with a chemical formula $C_xH_{2x}$, distinguished from other mono-olefins with a similar molecular formula by linearity of the hydrocarbon chain and the position of the double bond at the primary or alpha position. Linear alpha olefins comprise a class of industrially important alpha-olefins, including 1-butene, 1-hexene, 1-octene, 1-decene, 1-dodecene, 1-tetradecene, 1-hexadecene, 1-octadecene and higher blends of $C_{20}$-$C_{24}$, $C_{24}$-$C_{30}$, and $C_{20}$-$C_{30}$ olefins. Linear alpha olefins are very useful intermediates for the manufacture of detergents, synthetic lubricants, copolymers, plasticizers, and many other important products. Existing processes for the production of linear alpha olefins typically rely on the oligomerization of ethylene.

Linear alpha olefins can be prepared by the catalytic oligomerization of ethylene in the presence of a Ziegler-Natta-type catalyst or non-Ziegler-Natta-type catalyst. Important considerations of the ethylene oligomerization are the desired selectivity and the desired product distribution.

Oligomerization can occur at temperatures of 10 to 200° C., for example, 20 to 100° C., for example, 50 to 90° C., for example, 55 to 80° C., for example, 60 to 70° C. Operating pressures can be 1 to 5 MegaPascals (MPa), for example, 2 to 4 MPa. The process can be continuous and mean residence times can be 10 minutes to 20 hours, for example 30 minutes to 4 hours, for example, 1 to 2 hours. Residence times can be chosen so as to achieve the desired conversion at high selectivity.

The process can be conducted in solution using an inert solvent which can desirably be non-reactive with the catalyst composition. Alternatively, the process can be conducted in the presence of a solvent comprising a liquid alpha olefin, for example, $C_6$-$C_{100}$ alpha olefins. Solvents for use in the process can include, but are not limited to, aromatic or aliphatic hydrocarbons and halogenated aromatics such as chlorobenzene, dichlorobenzene, chlorotoluene, and combinations comprising at least one of the foregoing. For example, the solvents can include toluene, xylenes, $C_3$-$C_{24}$ alkanes, and combinations comprising at least one of the foregoing. For example, the solvent can be toluene.

The process can be carried out in any reactor, for example, a loop reactor, a plug-flow reactor, or a bubble column reactor. Oligomerization of ethylene is an exothermic reaction that can be cooled by a surplus flow of ethylene. A multipoint temperature measurement within the two-phase level can allow for detection of a thermal gradient. The gases leaving at a top portion of the reactor can be cooled using a series of external coolers and condensers. The gas phase, after further cooling, can be recycled.

A bottom stream leaving the oligomerization reactor from a bottom portion can contain the active catalyst and unreacted ethylene. The reaction can be terminated to avoid undesirable side reactions by removing catalyst components from the organic phase through extraction with a caustic aqueous phase. Contact with the caustic aqueous phase can result in formation of nonreactive minerals corresponding to the catalyst components.

The organic phase, after passage through the catalyst removal system, can pass through a molecular sieve absorption bed and can then be fed to a distillation column to recover dissolved ethylene. Recovered ethylene can be recycled via an ethylene recycle loop while the product is fed to an intermediate vessel, after which the product can be fed to a separation section.

The feedstock used can be pure ethylene or mixtures of ethylene with inert gases. Optionally, very minor proportions of other olefins can be present, but these can cause the production of unwanted olefin copolymers with attendant loss of conversion and linearity.

The present disclosure is further directed to a polyethylene product comprising linear alpha olefins made by the above-described process. For example, a polyethylene can be derived from the linear alpha olefin product made by the disclosed process. Alpha olefins of high purity are particularly valuable in the production of polyethylene, for example, linear low density polyethylene. The improved purity and linearity of the linear alpha olefins made by the disclosed process can eliminate problems in polyethylene formation, for example with regard to the presence of branched or internal olefins that can lead to subtle differences in the properties of the resulting polyethylene product, which can generally be undesirable.

The linear alpha olefins produced from the reactor can be directed into the separation train while the reactor equipment is flushed with an appropriate solvent, such as toluene. Examples of desirable organic solvents can include, but are not limited to, aromatic hydrocarbon solvents which can be unsubstituted or substituted, for example, toluene, benzene, ethyl benzene, xylene, mesitylene, monochlorobenzene, dichlorobenzene, chlorotoluene, aliphatic paraffin hydrocarbons, for example, pentane, hexane, heptane, octane, nonane, decane, alicyclic hydrocarbon compounds, for example, cyclohexane, decahydronaphthalene, and halogenated alkanes, for example, dichloroethane and dichlorobutane, or a combination comprising at least one of the foregoing. In some embodiments, the solvent can be toluene, xylene, mesitylene, ethyl benzene, n-pentane, n-hexane, cyclohexane, or a combination comprising at least one of the foregoing.

The produced linear alpha olefins can include $C_4$-$C_{20}$ linear alpha olefins. The flushed toluene including the polymeric material can enter the separation train, wherein the polymeric material can be more soluble in at least one of the linear alpha olefins than the toluene. For example, the polymeric material can be solubilized in the $C_{20+}$ linear alpha olefins. When the separation train separates the linear alpha olefins, either individually, or in certain tiers (e.g., $C_4$-$C_{10}$ fraction, $C_{11}$-$C_{17}$ fraction, $C_{18}$-$C_{20}$ fraction, $C_{20+}$ fraction, or any other desired fraction), the polymeric material can be soluble in the $C_{20+}$ fraction. As a result, the remaining separated fractions of linear alpha olefins, as well as the toluene, can exit the separation train essentially free of polymeric material, since the $C_{20+}$ fraction contains the polymer material. The linear alpha olefins in the separation train can be heated to at least 90° C., for example, at least 100° C., or for example, at least 110° C., wherein the linear alpha olefins can be heated to less than 200° C., for example, less than 180° C., or for example, less than 150° C.

Particularly advantageous is the fact that the toluene used in the flushing can be recovered at high purity without having to be subjected to a separate purification or recovery unit. By not having to separately purify and recover the toluene used in the flushing, cost savings can be achieved and efficiency of the overall process improved. Further, the percent recovery of the toluene used in the flushing can be improved in comparison to systems that implement a separate toluene recovery unit. For example, the methods disclosed herein can recover greater than 95% of the toluene used in the flushing, and in some examples greater than 99% recovery, e.g., 100% recovery. As a result, the methods are more efficient and economical, as the toluene in the solvent source does not need to be constantly replenished. Overall energy consumption can also be reduced in the process. For example, overall energy consumption can be reduced by greater than or equal to 100 MegaWatt-hours per year (MWh/yr), for example, greater than or equal to 125 MWh/yr, for example, greater than or equal to 150 MWh/yr, for example, greater than or equal to 170 MWh/yr. In an example, the recovery unit, which consumes 170 MWh/yr can be reduced with implementing the current method, resulting in a power consumption for recovery of 0 MWh/yr.

As illustrated in FIG. 1, the system 10 can include a reactor 12, a toluene source 14, and a separation train 16. Reactants 18, such as ethylene, solvent, and a catalyst can be fed into the reactor 12 to produce linear alpha olefins and a polymeric by-product material. After the reaction, a discharge stream 20 can be directed into the separation train 16, wherein the discharge stream can include unreacted reactants, the produced linear alpha olefins, such as $C_4$-$C_{20+}$, solvent, and catalyst. The separation train 16 can be configured to separate the linear alpha olefins from the solvent, catalyst, and any unreacted ethylene. The separation train 16 can separate each linear alpha olefin, for example, yielding a $C_4$ stream, $C_5$ stream, $C_6$ stream, and so on. The separation train 16 can also separate the linear alpha olefins into certain fractions, such as $C_4$-$C_{10}$ fraction, $C_{11}$-$C_{17}$ fraction, $C_{18}$-$C_{20}$ fraction, $C_{20+}$ fractions, or any other desired fraction.

After the reaction, the reactor 12 can be flushed with toluene from the toluene source 14 to remove the polymeric by-product buildup in the reactor equipment. The flushed toluene containing the polymeric material can be directed into the separation train 16 via line 22. Of course, the flushed toluene can exit the reactor through line 20, such that the system does not require two separate exiting lines from the reactor 12. Because the polymeric material is more soluble in the $C_{20+}$ linear alpha olefins than toluene, the polymeric material can be separated from the flushed toluene and the $C_4$-$C_{18}$ fractions by dissolving into the $C_{20+}$ linear alpha olefins. As a result, the flushed toluene separated in the separation train 16 can be recycled back to the toluene source for further flushing without needing further purification.

Utilizing the present systems and methods allows the reactor equipment including the piping to be efficiently and cost effectively cleaned so as to maintain large pump flow rates. The present methods can avoid the use of a separate purification system for the toluene used in flushing the reactor equipment. Further, the toluene used in the flushing is essentially fully recovered, avoiding the necessity of replenishing the solvent for subsequent flushes.

The article of manufacture and methods of making disclosed herein include at least the following embodiments:

Embodiment 1

A method of flushing a reactor used in the production of linear alpha olefins, comprising: flushing reactor equipment used in the production of linear alpha olefins, with toluene from a solvent source, wherein the reactor contains by-products from the production of the linear alpha olefins, wherein the by-products include a polymeric material; directing the flushed toluene containing polymeric material into a separation train containing the linear alpha olefins, wherein the polymeric material is soluble in at least one of the linear alpha olefins; separating the linear alpha olefins from the toluene; and recycling the toluene to the solvent source.

Embodiment 2

The method of Embodiment 1, wherein greater than 95% of the toluene used in the flushing is recycled to the solvent source.

Embodiment 3

The method of Embodiment 1 or Embodiment 2, wherein greater than 99% of the toluene used in the flushing is recycled back to the solvent source.

Embodiment 4

The method of any of Embodiments 1-3, wherein the linear alpha olefins include at least one of a $C_4$ to $C_{20+}$ linear alpha olefin.

Embodiment 5

The method of any of Embodiments 1-4, wherein the linear alpha olefins include a $C_{20+}$ linear alpha olefin, wherein the polymeric material is soluble in the $C_{20+}$ linear alpha olefin.

Embodiment 6

The method of any of Embodiments 1-5, wherein the linear alpha olefins are heated to at least 90° C. in the separation train.

Embodiment 7

The method of any of Embodiments 1-6, wherein the recycled toluene is free of polymeric material.

Embodiment 8

The method of any of Embodiments 1-7, wherein the recycled toluene is free of linear alpha olefins.

Embodiment 9

The method of any of Embodiments 1-8, wherein the linear alpha olefins include at least one of a $C_4$ to $C_{20+}$ linear alpha olefin, wherein the separation train separates each of the at least one of $C_4$ to $C_{20+}$ linear alpha olefins.

Embodiment 10

A method for producing linear alpha olefins, comprising: feeding ethylene, a solvent, and a catalyst into a reactor; oligomerizing ethylene in the reactor to produce linear alpha olefins and a polymeric material; directing the reactor effluent comprising the linear alpha olefins, solvent, and unreacted ethylene into a separation train configured to separate the linear alpha olefins from the solvent and unreacted ethylene; flushing the reactor with toluene from a toluene source, wherein the flushed toluene contains the polymeric material; directing the flushed toluene into the separation train, wherein the polymeric material is soluble in at least one of the linear alpha olefins; recycling the toluene to the toluene source; and recycling the separated unreacted ethylene and solvent to the reactor.

Embodiment 11

The method of Embodiment 10, wherein the linear alpha olefins include at least one of a $C_4$ to $C_{20+}$ linear alpha olefin.

Embodiment 12

The method of Embodiment 10 or Embodiment 11, wherein the linear alpha olefins include a $C_{20+}$ linear alpha olefin.

Embodiment 13

The method of any of Embodiments 10-12, wherein the linear alpha olefins include at least one of a $C_4$ to $C_{20+}$ linear alpha olefin, wherein the separation train separates each of the at least of $C_4$ to $C_{20+}$ linear alpha olefins.

Embodiment 14

The method of any of Embodiments 10-13, wherein greater than 95% of the toluene used in the flushing is recycled to the toluene source.

Embodiment 15

The method of any of Embodiments 10-14, wherein greater than 99% of the toluene used in the flushing is recycled back to the toluene source.

Embodiment 16

The method of any of Embodiments 10-15, wherein the linear alpha olefins include a $C_{20+}$ linear alpha olefin, wherein the polymeric material is soluble in the $C_{20+}$ linear alpha olefin.

Embodiment 17

The method of any of Embodiments 10-16, wherein the linear alpha olefins are heated to at least 90° C.

Embodiment 18

The method of any of Embodiments 10-17, wherein the recycled toluene is free of polymeric material.

Embodiment 19

The method of any of Embodiments 10-18, wherein the recycled toluene is free of linear alpha olefins.

Embodiment 20

The method of any of Embodiments 10-19, wherein the flushed toluene is directly directed into the separation train, wherein the separated toluene from the separation train is directly directed into the toluene source.

Embodiment 21

The method of any of Embodiments 1-19, wherein the overall energy consumption is reduced by greater than or equal to 100 MegaWatt-hours per year.

Embodiment 22

The method of any of Embodiments 1-20, wherein the overall energy consumption is reduced by greater than or equal to 170 MegaWatt-hours per year.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method of flushing a reactor used in the production of linear alpha olefins, comprising:
    flushing reactor equipment used in the production of linear alpha olefins, with toluene from a solvent source, wherein the reactor equipment contains by-products from the production of the linear alpha olefins, wherein the by-products include a polymeric material;
    directing the flushed toluene containing polymeric material into a separation train containing the linear alpha olefins, wherein the polymeric material is soluble in at least one of the linear alpha olefins;
    separating the linear alpha olefins from the toluene; and
    recycling the toluene to the solvent source.

2. The method of claim 1, wherein greater than 95% of the toluene used in the flushing is recycled to the solvent source.

3. The method of claim 2, wherein the linear alpha olefins include at least one of a $C_4$ to $C_{20+}$ linear alpha olefin.

4. The method of claim 1, wherein greater than 99% of the toluene used in the flushing is recycled back to the solvent source.

5. The method of claim 1, wherein the linear alpha olefins include a $C_{20+}$ linear alpha olefin, wherein the polymeric material is soluble in the $C_{20+}$ linear alpha olefin.

6. The method of claim 1, wherein the linear alpha olefins are heated to at least 90° C. in the separation train.

7. The method of claim 1, wherein the recycled toluene is free of polymeric material.

8. The method of claim 1, wherein overall energy consumption can be reduced by greater than or equal to 100 MegaWatt-hours per year.

9. The method of claim 1, wherein the linear alpha olefins include at least one of a $C_4$ to $C_{20+}$ linear alpha olefin, wherein the separation train separates each of the at least one of $C_4$ to $C_{20+}$ linear alpha olefins.

10. A method for producing linear alpha olefins, comprising:

feeding ethylene, a solvent, and a catalyst into a reactor;

oligomerizing ethylene in the reactor to produce linear alpha olefins and a polymeric material;

directing the reactor effluent comprising the linear alpha olefins, solvent, and unreacted ethylene into a separation train configured to separate the linear alpha olefins from the solvent and unreacted ethylene;

flushing the reactor with toluene from a toluene source, wherein the flushed toluene contains the polymeric material;

directing the flushed toluene into the separation train containing the linear alpha olefins, wherein the polymeric material is soluble in at least one of the linear alpha olefins;

recycling the toluene to the toluene source; and recycling the separated unreacted ethylene and solvent to the reactor.

11. The method of claim 10, wherein the linear alpha olefins include at least one of a $C_4$ to $C_{20+}$ linear alpha olefin.

12. The method of claim 10, wherein the linear alpha olefins include a $C_{20+}$ linear alpha olefin.

13. The method of claim 10, wherein the linear alpha olefins include at least one of a $C_4$ to $C_{20+}$ linear alpha olefin, wherein the separation train separates each of the at least of $C_4$ to $C_{20+}$ linear alpha olefins.

14. The method of claim 10, wherein greater than 95% of the toluene used in the flushing is recycled to the toluene source.

15. The method of claim 10, wherein greater than 99% of the toluene used in the flushing is recycled back to the toluene source.

16. The method of claim 10, wherein the linear alpha olefins include a $C_{20+}$ linear alpha olefin, wherein the polymeric material is soluble in the $C_{20+}$ linear alpha olefin.

17. The method of claim 10, wherein the linear alpha olefins are heated to at least 90° C.

18. The method of claim 10, wherein the recycled toluene is free of polymeric material.

19. The method of claim 10, wherein overall energy consumption is reduced by greater than or equal to 170 MegaWatt-hours per year.

20. The method of claim 10, wherein the flushed toluene is directly directed into the separation train, wherein the separated toluene from the separation train is directly directed into the toluene source.

* * * * *